United States Patent [19]
Holen

[11] Patent Number: 5,814,331
[45] Date of Patent: Sep. 29, 1998

[54] PROCESS FOR INHIBITING PATHOGENIC BACTERIA IN THE ORAL CAVITY AND FOR BINDING PEPTIDE GROWTH FACTORS ON SURFACES

[76] Inventor: Sheldon Holen, 2928 Macomb St. NW., Washington, D.C. 20008

[21] Appl. No.: 542,588

[22] Filed: Nov. 13, 1995

[51] Int. Cl.⁶ .............................. A61K 6/00; A61K 31/65
[52] U.S. Cl. .............................................. 424/435; 424/54
[58] Field of Search ........................................ 424/54, 435

[56] References Cited

U.S. PATENT DOCUMENTS

| | | |
|---|---|---|
| 3,991,766 | 11/1976 | Schmitt et al. . |
| 4,442,133 | 4/1984 | Greco et al. . |
| 4,740,382 | 4/1988 | Greco et al. . |
| 4,764,377 | 8/1988 | Goodson . |
| 4,879,135 | 11/1989 | Greco et al. . |
| 4,889,720 | 12/1989 | Konishi . |
| 5,084,267 | 1/1992 | Damani . |
| 5,114,718 | 5/1992 | Damani . |
| 5,173,299 | 12/1992 | Damani . |
| 5,186,936 | 2/1993 | Groves . |
| 5,196,202 | 3/1993 | Konishi . |
| 5,197,882 | 3/1993 | Jernberg . |
| 5,230,895 | 7/1993 | Czarnecki et al. . |
| 5,300,290 | 4/1994 | Spencer ...................................... 424/54 |
| 5,324,520 | 6/1994 | Dunn et al. . |
| 5,356,433 | 10/1994 | Rowland et al. . |

FOREIGN PATENT DOCUMENTS 2116214  10/1971  Germany .

*Primary Examiner*—Peter F. Kulkosky
*Attorney, Agent, or Firm*—Donald C. Casey, Esq.

[57] ABSTRACT

A process for inhibiting the growth of pathogenic bacteria and aiding in periodontal tissue healing within the oral cavity by binding therapeutic agents to surfaces is described. The process includes initial coating of hard surfaces in the oral cavity such as tooth roots, dental restorative materials, dental implants, and guided tissue regeneration surgery barrier membranes with a cationic surfactant, tridodecylmethylammonium chloride, and then binding antibiotics such as tetracycline, metronidazole or with Platelet Derived Growth Factor. These surfaces are thereby made unavailable for bacterial colonization. Tooth roots, barrier membranes and other materials used in regenerative periodontal surgery also may be coated with cationic surfactant to bind local or added platelet derived growth factors.

9 Claims, 1 Drawing Sheet

PROCESS FOR INHIBITING PATHOGENIC BACTERIA IN THE ORAL CAVITY AND FOR BINDING PEPTIDE GROWTH FACTORS ON SURFACES

TECHNICAL FIELD

This invention relates to the application of therapeutic agents (antimicrobials and platelet derived growth factors) to fight infection and promote healing in the oral cavity. More particularly, this invention relates to a process for facilitating retention of antimicrobial agents on surfaces within the oral cavity and also on barrier membranes placed under the gums in guided tissue regeneration surgical procedures, denying these surfaces for bacterial colonization. The purpose is to inhibit growth of pathogenic bacteria on tooth roots, dental restorations, and dental implants, and also, to protect the submerged barrier membranes from infection and subsequent rejection. This invention also facilitates the retention of platelet derived growth factor on tooth root surface, on dental implant surface, and on guided tissue regeneration membranes to enhance the healing process.

BACKGROUND ART

The formation of dental plaque containing disease causing bacteria on the surfaces of teeth and dental restorations has long been acknowledged as the prime cause of gingivitis and periodontitis. Destruction of the supporting tissues of the natural teeth and the supporting bone of dental implants is the result of infection caused by colonization of pathogenic bacteria, most of which are susceptible to the antibacterial effects of tetracycline and metronidazole. The non-surgical treatment of periodontal diseases is directed toward removal of disease causing bacteria from the tooth surfaces and the surgical treatment is directed at reducing hard surface areas for attachment of these infective formations. Neither treatment can be very successful without elimination or suppression of the pathogenic bacteria.

While periodontal treatment and good oral hygiene help reduce the disease causing organisms, they do not necessarily prevent re-infection. Systemic antibiotics, single agents and combinations of agents, are frequently used as an adjunct in periodontal treatment, but it is known to be preferable to use antibiotics locally. There has been a great deal of research aimed at developing drug delivery devices for local application of antimicrobials to combat these tenacious groups of bacteria in the periodontal space but they have yield only limited success. The evolving art in this area is the placement of collagen membranes, gels, microchips, and various absorbable polymer compositions in the periodontal pocket to carry the therapeutic agent for release (U.S. Pat. Nos. 3,991,766, 4,764,377, 4,889,720; 5,084,267,5,114,718; 5,173,299; 5,186,936; 5,196,202; 5,197,882; 5,230,895; 5,324,520).

Recent developments in the art have been directed toward delivering tetracycline to the periodontal pocket (the infected space between the tooth and the gum) with a controlled release polymer cord (U.S. Pat. Nos. 5,084,267, 5,173,299 and 5,114,718). The use of this device requires careful professional placement of the cord and gluing it to place. It is to be kept in place for 7 to 10 days, and than requires professional personnel removal. Although many pathogenic bacteria are affected by tetracycline during this time, it is not effective against all of the bacteria infecting periodontal pockets. Retention of the fiber in the site is problematic. The use of controlled delivery devices for an antimicrobial agent is limited by three local factors: the resistance of many periodontal pathogens to single chemotherapeutic agents, low volume of crevicular fluid in the pocket to accept the agent, and a high turnover rate of that crevicular fluid and surrounding saliva (M. Goodson, "Pharmmakinetic Principles Controlling Efficiency of Oral Therapy," *J. Dent. Res.* 1989; 68 [Special Issue] : 1625–32).

The process described herein seeks over come these limitations of bacterial suppression by making surfaces unavailable of colonization and growth rather than as a method of drug delivery as referenced by the above.

Surgical techniques aiming for regeneration of lost periodontal support for teeth, for healing lost supporting bone around dental implants, and for augmentation of the jaw bone so that dental implants can be placed utilize barrier membranes, meant to be in place for 4 to 6 weeks, for guiding healing tissues. These procedures loose their efficaciousness when the membranes become contaminated with oral bacteria and must be removed in the early post-operative period.

In U.S. Pat. No. 4,879,135, and related U.S. Pat. Nos. 4,442,133 and 4,740,382, there is reported the use of a cationic surfactant, tridodecymethyl-ammonium chloride (TDMAC), as a coating for vascular prostheses and implantable devices to provide sites for antibiotic bonding so that the prostheses will exhibit resistance to infection in the peri-operative period. In that case the drug was an antibiotic suitable for blood borne pathogens that colonize the surfaces of biomaterials and/or an antithrombotic agent. In that case the prostheses were treated for 30 minutes with TDMAC and placed in the antibiotic solutions for one hour. The process was designated for prostheses that were defined as implantable devices to include catheters, vascular grafts, shunts, penile prostheses, heart valves, orthopedic prostheses, intraocular prostheses, and sutures. Although tetracycline was mentioned as a possibility for TDMAC binding, it is listed as a neutral compound, not the highly anionic molecule an elevation of pH produces. Metronidazole is not mentioned, nor are combinations of antibiotics mentioned.

These references to surfactant binding do not utilize the process described herein with its brief application times, its application in the mouth, its application on a biologic structure, i.e. a tooth root, its application on dental restorative materials in the mouth, or its application to the unique environment found in the oral cavity. U.S. Pat. No. 5,356,433 covers the use of surfactant mediated binding to metallic surfaces of medical devices or components of medical devices to enhance biocompatability by binding an organosilane compound which will then bind other biologic agents. All claims relate to a flexible tantalum splint and there is no mention of antibiotics or dental applications.

The effectiveness of tetracycline and metronidazole, alone or in combinations, against many of the aerobic and anaerobic pathogenic oral bacteria is well known (C. Walker et al., "Antibiotic susceptibilities of Periodontal Bacteria." *J. Periodont.* 1985; 56 [Suppl.]: 67–74). Tetracycline and its derivatives are active in vitro against *A. actinomycetemcomitas, E. coli, P. gingivalis, P. intermedia, P. micros,* and *C. rectus.* Even sublethal concentrations of tetracycline have also been shown to limit the adherence and coaggregation of pathogenic bacteria (W. Peros et al., "Alterations of Fimbriation and Cell Hydrophobicity by Sublethal Concentrations of Tetracycline," *J. Periodont. Res.* 1985; 20:24–30) which will retard their colonization on surfaces.

In addition to these antimicrobial effects, tetracycline also has the propriety of blocking the tissue destructive effects of the metalloprotinases, collagenase and elastase, from bacteria and inflamed tissues which destroy the support of the teeth. (B. Rifkin et al., "Blocking Periodontal Disease Progression by Inhibiting Tissue Destructive Enzymes: A Potential Therapeutic Role for Tetracyclines and their Chemically-Modified Analogs", *J. Periodont.*, 64:8, August 1993, [suppl.]).

The application of platelet-derived growth factors (PDGF) in an aqueous gel has been shown to be effective in improving connective tissue regeneration when placed in the surgical site during regenerative periodontal surgical procedures. Its effectiveness may be limited by its rapid removal from the surgical site (M. Cho, et al., "Platelet Derived Growth Factor-Modulated Guided Tissue Regenerative Therapy", *J. Periodont. August,* 1995, 66:6, 522–31). This process applied to the root surface or barrier membranes can hold any added or locally produced PDGF.

SUMMARY OF THE INVENTION

It has been discovered that therapeutic amounts of tetracycline, alone or in combination with therapeutic amounts of metronidazole, can be bound to the roots of teeth, dental restorations, dental implant bodies, and barrier membranes of various materials utilized in guided tissue regeneration surgical procedures by a brief pre-treatment of the air dried surface with a 5% TDMAC solution in a lower alkyl hydrocarbon such as ethanol.

It has been discovered that these antibiotics bound in this way retain their antimicrobial activity while bound and do not have to released to prevent bacterial growth on the surface that binds them.

It has been discovered that these antibiotics can be retained on surfaces in conditions similar to the oral cavity for long periods of time without loss of antibiotic activity.

It has been discovered that when the pH of a solution of tetracycline is raised to above 9.3, all cationic binding sites become available so that in less than 1 minute substantial amounts of tetracycline are bound to a TDMAC treated surface.

It has been discovered that after tetracycline has been bound to a surfactant treated surface, metronidazole, in biologically significant amounts can than be complexed on that surface for long periods of time.

It has been discovered that tetracycline bound through surfactant to expanded polytetrafluoroethylene (e-PTFE) and other types of membranes used in guided tissue regeneration prevents their contamination and premature loss, thereby increasing the amount of periodontal regeneration.

It has been discovered that e-PTFE membranes treated with TDMAC bind up to 7 times more platelet derived growth factor from an acetic acid solution than untreated membranes.

Accordingly, it is the object of this invention to provide a process, suitable for use by professional dental personnel, for binding antimicrobial agents, tetracycline and metronidazole to surfaces disposed within the oral cavity so that antimicrobial agents will block or inhibit bacterial growth over a prolonged period of time.

It is another object of this invention to provide a therapeutic agent, antibiotic or peptide growth factor, to the surfaces of barrier membranes used in guided tissue regeneration surgical procedures to enhance their retention and improve healing.

These and other objects will become apparent with reference to the drawing and following description wherein:

BRIEF DESCRIPTION OF THE DRAWING

The FIGURE is a schematic representation of a tetracycline molecule.

DETAILED DESCRIPTION OF THE INVENTION

Figure 1:
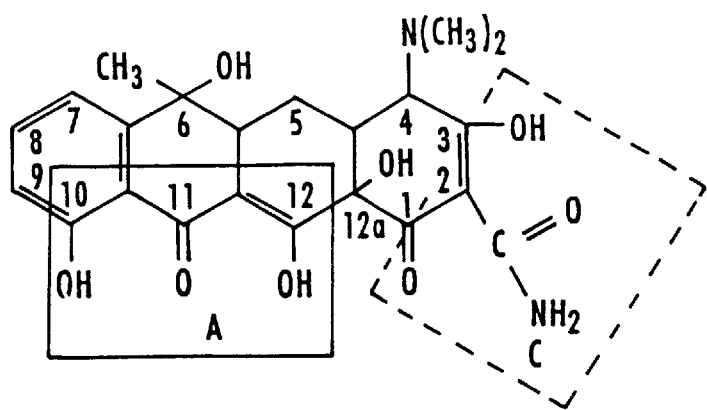

To facilitate an understanding of the present invention, the present invention will be described and explained with reference to the treatment of an infected periodontal space (pocket) which shows the classical signs of soft tissue inflammation and easy bleeding on probing. After careful removal adherent dental calculus and plaque, the area is isolated for drying and the root surface is air dried. A 5% ethanol solution of TDMAC is applied with a cotton ball, and the root is air dried. A fresh tetracycline hydrochloride solution, 50 mg/ml, whose pH is raised to above 9.3 by adding 1 N sodium hydroxide, is applied with a cotton ball. After 1 minute, it is air dried. Binding is indicated by a yellow color. Optionally, a saturated ethanol solution of metronidazole may be applied with a cotton ball for 1 minute and air dried.

On application and drying, a dilute solution of TDMAC in ethanol forms a uniformly oriented layer or layers that present positively charged binding sites for the multiple negative sites of the charged tetracycline molecule. This results in the binding of the non-antibiotic portion which aligns the antibiotic portion of the molecule facing away from the root surface. Metronidazole is probably complexed by underutilized TDMAC sites.

With reference to the Figure, the preferred therapeutic agent of this invention is tetracycline which is a naphacene carboxamide compound with an A ring and constituents rotated with respect to the plane of the B-C-D ring. The ability of substantial amounts of tetracycline to be bound and retained to TDMAC treated surfaces is probably a function of the cationic binding sites at carbon atoms 1, 2, 3, 10, 11, and 12 which become active at pH 7.5 and the dimethylamino group that becomes partially depronated at a pH above 9.3, enabling the complexation with an additional two cations. Therefore, at a pH above 9.3, all seven sites are involved in binding a normally amphoteric molecule securely to the surfactant cationic binding sites. It was discovered that none of this binding activity affected the antimicrobial activity of the tetracycline molecule.

Retention of the bound tetracycline in an environment similar to the oral cavity was demonstrated by In vito experiments. Membranes of e-PTFE were coated with tetracycline in the described manner and placed in pooled human serum for two weeks. Aliquots of the serum were drawn and examined for tetracycline that had come off the membranes. It was found that after some early loss, no further tetracycline was released in the serum, demonstrating retention on the membranes (Table 1). After 1 month, the membranes were placed in an agar plate with a maintained plaque culture and found to be antibacterial by a clear Zone of Bacterial Inhibition after growth had occurred.

TABLE 1

| Tetracycline Debinding in Serum | |
|---|---|
| Incubation Time | Tetracycline/ml |
| 1 h | 1.9 mg |
| 7 h | 3.7 mg |

TABLE 1-continued

Tetracycline Debinding in Serum

| Incubation Time | Tetracycline/ml |
|---|---|
| 24 h | 3.6 mg |
| 3 days | 3.6 mg |
| 8 days | 3.6 mg |
| 14 days | 3.5 |

Metronidazole [1-(2-hydroxyethyl 1)-2-methyl-5-nitroimidazole] and its hydroxyl metabolite (the addition of a 2nd hydroxyl group) is active against Bacteroides and other anaerobic pathogens. These hydroxyl groups provide binding opportunities for the TDMAC layer and the tetracycline molecule. Complexation by hydrophobic interactions may also occur.

These treatments were verified in vitro on sections of the roots of 20 freshly extracted teeth and on 10 Brânemark polished titanium implants which were treated as described for teeth in the mouth. The teeth and the implants retained their antimicrobial potency against periodontal disease pathogens after two weeks of immersion in 100 ml of saline, as observed by the clear Zone of Bacterial Inhibition in agar medium of periodontal pathologic bacteria. There was no inhibition of bacterial growth with untreated specimens or specimens treated only with TDMAC.

To facilitate an understanding of another application of the present invention, the present invention will be described with reference to a guided tissue regeneration surgical procedure. At the time of surgery, after the type and shape of the barrier membrane needed is apparent, it is dipped in a 5% ethanol solution of TDMAC and air dried. It is then placed in a fresh solution of tetracycline hydrochloride, whose pH has been raised above 9.3 with 1 N sodium hydroxide, air dried. The unbound tetracycline is removed with a water wash. When the membrane dries, after an additional 1 minute bath of ethanol solution, metronidazole may be added.

In clinical investigation, 30 patients with 30 periodontitis created osseous defects were randomly treated as a part of periodontal tissue regeneration surgery with tetracycline coated e-PTFE membranes (test) or non-coated e-PTFE membranes (control). The maximal depth of the defects were determined at the time of membrane placement and at the second stage surgery when the membranes were removed. Microbial examination of the membranes was done at the time of their insertion and their removal. This study found enhanced clinical benefits with the use of tetracycline coated membranes in defect resolution. (Nowzari, et al., "In vitro and in vivo Antimicrobial Activity of Tetracycline Coated e-PTFE Barrier Membranes Used in Guided Bone Regeneration") accepted for publication in Compendium of Continuing Education, University of Pennsylvania.

The use of this process to preferentially bind platelet derived growth factors (PDGF) to barrier membranes and teeth roots to provide for prolonged concentration of these factors at the time of regenerative periodontal surgery was demonstrated in vitro. e-PTFE material treated with a 5% TDMAC solution in 95% ethanol was placed in a standard solution of radiolabeled PDGF in acetic acid. After 15 and 45 minutes, the material was washed and the residual tagged PDGF was measured (Table 2).

| Material Treatment | Incubation Time | |
|---|---|---|
|  | 15 min. | 45 min. |
| Control | 926 | 1515 |
| TDMAC Coating | 6891 | 9448 |

The purpose of the above description and examples is to illustrate some embodiments of the present invention without implying any limitation. It will be apparent to those of skill in the art that various modifications and variations may be made to the device and method of the present invention without departing from the spirit or scope of the invention.

I claim:

1. A process for inhibiting bacterial growth in the oral cavity by occupying bacterial growth sites comprising the steps of:

selecting a surface within the oral cavity or on a substrate to be introduced into the oral cavity said surface being a member selected from the group consisting of teeth, crowns, pontics, connectors screws titanium or hydroxyapatite coated titanium implants or polytetrafluoroethylene membranes: providing the surfactant, tridodecylemthylammonium chloride in solvent in about a 5% solution and applying said surfactant to said surface and subsequently applying a solution of the therapeutic agent tetracycline, at a pH of at least 9.3 to said surfactant coated surface wherein bound tetracycline is retained in an environment similar to the oral cavity.

2. The process of claim 1, wherein said solvent is ethanol.

3. The process of claim 1, where the surfactant coated surface is dry when it is covered with the therapeutic agent.

4. The process of claim 1 wherein said agent is tetracycline, said process further comprising covering said agent coated surface, wherein bound metronidazole is retained in an environment similar to the oral cavity with a saturated metronidazole solution and subsequently air drying said covered surface.

5. The process of claim 4, wherein said metronidazole is present as a saturated solution in ethanol.

6. A process for inhibiting bacterial growth in the oral cavity by occupying bacterial growth sites comprising the steps of:

selecting a surface wherein bound metronidazole is retained in an environment similar to the oral cavity within the oral cavity or on a substrate to be introduced into the oral cavity said surface being a member selected from the group consisting of teeth, crowns, pontics, connectors, screws titanium or hydroxyapatite coated titanium implants or polytetraflouoroethylene membranes: providing the surfactant tridodecylmethylammonium chloride in an organic solvent in about a 5% solution; and applying said solution to said surface subsequently applying a solution of the therapeutic agent Platelet Derived Growth Factor to said surfactant coated surface, wherein bound Platelet Derived Growth Factor is retained in an environment similar to the oral cavity.

7. The process of claim 6 wherein said solvent is ethanol.

8. The process of claim 6 wherein said agent is present as a saturated solution in ascetic acid.

9. The process of claim 6 wherein said substrate is expanded polytetrafloroethylene.

* * * * *